United States Patent [19]
Karas

[11] Patent Number: 5,994,578
[45] Date of Patent: Nov. 30, 1999

[54] ESTER PREPARATION

[75] Inventor: Lawrence J. Karas, West Chester, Pa.

[73] Assignee: Arco Chemical Technology, L.P., Greenville, Del.

[21] Appl. No.: 09/022,183

[22] Filed: Feb. 11, 1998

Related U.S. Application Data

[63] Continuation-in-part of application No. 08/816,704, Mar. 13, 1997, abandoned.

[51] Int. Cl.$^6$ .................................................. C07C 67/04
[52] U.S. Cl. ................................................ 560/247
[58] Field of Search ............................................ 560/247

[56] References Cited

U.S. PATENT DOCUMENTS

| | | |
|---|---|---|
| 2,678,332 | 5/1954 | Cottle et al. . |
| 3,031,495 | 4/1962 | Young et al. . |
| 3,037,052 | 5/1962 | Bortnick . |
| 3,172,905 | 3/1965 | Eckert . |
| 3,173,943 | 3/1965 | Hess et al. . |
| 3,678,099 | 7/1972 | Kemp . |

OTHER PUBLICATIONS

Pavlov et al. General Preparative Method for The Esterification of Carboxylic Acids with Isobutylene in the Presence of Tert–Butanol Bull Soc. Chem Fr. No. 12 p. 2985–2986 (1974).

*Primary Examiner*—Michael L. Shippen
*Attorney, Agent, or Firm*—William C. Long

[57] ABSTRACT

An olefin such as isobutylene is reacted with a carboxylic acid to produce the ester in the presence of a modifying agent effective to suppress olefin polymerization, the feed to the reaction containing not more than 0.7 mols water per mol of olefin.

2 Claims, 1 Drawing Sheet

ESTER PREPARATION

RELATED APPLICATION

This application is a continuation-in-part of copending application Ser. No. 08/816,704 filed Mar. 13, 1997 now abandoned.

BACKGROUND OF THE INVENTION

1. Field of the Invention

The present invention provides an improved method for the preparation of esters such as t-butyl acetate.

2. Description of the Prior Art

It is known to produce esters by the reaction of an olefin such as isobutylene with a lower carboxylic acid over a sulfonate group-containing cation exchange resin. See U.S. Pat. No. 3,678,099 and the references disclosed therein including U.S. Pat. Nos. 2,678,332, 3,031,495, 3,172,905 and 3,173,943.

A problem which is encountered in such prior procedures has been the tendency for polymerization of the olefin to occur during the esterification which results both in significant yield losses and in the formation of products such as olefin dimer which are difficult to separate from the product ester. For example, isobutylene dimer forms an azeotrope with t-butyl acetate thus making separation exceedingly difficult.

Work has been performed with sulfuric acid as a catalyst. See, for example Pavlov et al., "GENERAL PREPARATIVE METHOD FOR THE ESTERIFICATION OF CARBOXYLIC ACIDS WITH ISOBUTYLENE IN THE PRESENCE OF TERT-BUTANOL", BULL soc. Chem Fr4. No. 12 P 2985–6 (1974). This reference describes the use of tertiary butanol in the sulfuric acid catalyzed system to suppress isobutylene polymerization. The sulfuric acid catalyst system has severe inherent difficulties associated with corrosion, problems of catalyst separation and recovery, and the tendency for side reactions.

U.S. Pat. No. 4,011,272 relates to a method for the production of tertiary butyl alcohol by reaction of isobutylene with water in the presence of a sulfonic acid resin and an organic acid such as acetic acid. Water is used in at least equimolar amount relative to the isobutylene and tertiary butyl alcohol is the primary product. The patent teaches that the minor amounts of tertiary butyl acetate which are formed can readily be hydrolyzed to form additional tertiary butyl alcohol.

BRIEF DESCRIPTION OF THE INVENTION

In accordance with the invention, olefin dimer production in the reaction between olefin and lower carboxylic acid to form predominantly the ester is reduced by carrying out the reaction in the presence of a selectivity enhancing modifier such as t-butyl alcohol.

DESCRIPTION OF THE DRAWING

The attached drawing illustrates an embodiment of the invention.

DETAILED DESCRIPTION

Figure 1:
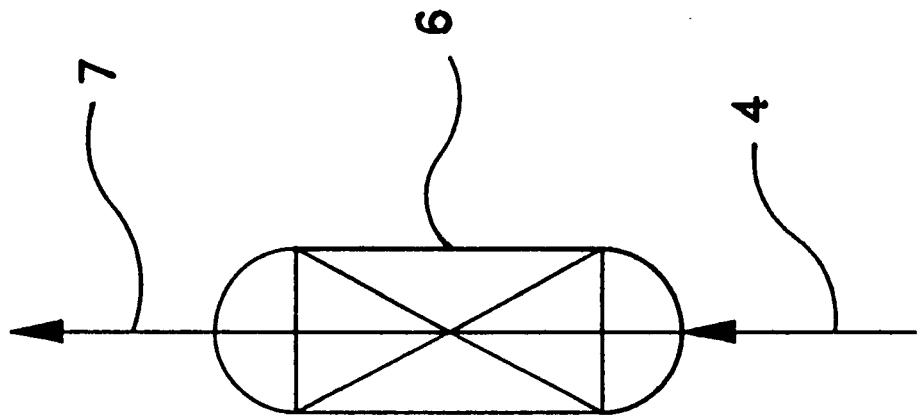

The present invention, although applicable generally to the formation of esters having the formula

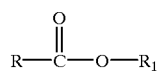

wherein $R_1$ is a $C_1$–$C_{10}$ alkyl group and R is hydrogen or a $C_1$–$C_{10}$ alkyl group, is especially applicable to the formation of esters wherein $R_1$ is a $C_4$ or $C_5$ tertiary alkyl group and R is hydrogen or a $C_1$–$C_2$ alkyl group. T-butyl acetate is an especially preferred product.

In accordance with the invention, olefin and organic carboxylic acid are reacted to form predominantly the ester over a solid acidic catalyst in the presence of a modifying agent which enhances the selectivity of the ester formation reaction while suppressing the formation of olefin polymer including olefin dimer. Especially preferred modifying agents are t-butyl alcohol and t-amyl alcohol, and the lower ($C_1$–$C_3$) ethers thereof such as methyl tertiary butyl ether, methyl tertiary amyl ether and the like.

The catalysts employed are known. See U.S. Pat. No. 3,678,099 the disclosure of which is incorporated herein by reference. Sulfonic acid-type exchange resins are especially useful as illustrated by Amberlyst A-15. Other known solid catalysts such as acidic zeolites, and clays, and the like can be used.

The reaction is most advantageously a continuous one carried out in the liquid phase at relatively mild temperatures, eg. 10–100° C., preferably 15–30° C. and sufficient pressure to maintain the liquid phase. Reaction temperatures below about 27° C. are especially preferred.

The mol ratio of olefin to carboxylic acid can vary widely, ratios of 0.1–10 mols olefin per mol carboxylic acid are generally useful, ratios of 0.1 to 0.5 mols olefin per mol carboxylic acid are especially useful. The higher amounts of acid relative to olefin improve reaction selectivity and further aid in suppressing dimer make.

As an important feature, it is necessary that the feed to the solid acidic catalyst catalyzed esterification reaction contain no more than about 0.7 mols of water per mol of olefin, preferably no more than 0.6 mols of water per mol of olefin and most preferably no more than 0.1 mols of water per mol olefin. This is radically different from the process of U.S. Pat. No. 4,011,272 where water is used in amount of at least 1.0 mol of water per mol of olefin, and wherein, the predominant reaction product is the alcohol and not the ester.

The selectivity enhancing modifying agent is used in the solid acidic catalyst catalyzed reaction in an amount by weight of the total reaction mixture of at least 2 wt %, preferably 4 to 40 wt %, and most preferably 6–12 wt %.

The following is a description of the embodiment for a continuous preparation of t-butyl acetate as illustrated in the accompanying drawing.

Referring to the drawing, the reaction feed mixture passes continuously via line 4 to reactor 6. Reactor 6 is a fixed bed reactor packed with acidic solid catalyst such as Amberlyst A-15. The composition of the reaction mixture which passes via line 4 to reactor 6 is such as to provide isobutylene and acetic acid in appropriate amounts for reaction to form t-butyl acetate as well as t-butanol in appropriate amount to act as modifying agent to enhance t-butyl acetate reaction selectivity while suppressing isobutylene polymerization. As above described, it is essential that the feed mixture contain not more than 0.7 mols of water per mol of isobutylene.

The reaction mixture passes continuously to reactor 6 wherein upon contact with the Amberlyst A-15 catalyst, reaction of isobutylene and acetic acid takes place with the formation of t-butyl acetate. Due to the effect of the t-butanol modifying agent, little or no polymerization of the isobutylene takes place in reactor 6 and at the low temperatures there is little or no dehydration of t-butanol.

The reaction mixture comprised of product t-butyl acetate, t-butanol, acetic acid, and isobutylene passes from reactor 6 via line 7 to conventional separation and recovery means.

The following examples illustrate the invention:

A series of continuous esterification runs were carried out using Amberlyst A-15 catalyst and reacting isobutylene and acetic acid to form t-butyl acetate; the runs were carried out at 100 psig. The following Tables 1 and 2 show the reaction conditions and the results obtained.

TABLE I

| Run | Reaction Temperature, Deg F. | Reactant Ratio AcOH/IB (mol/mol) | Modifier % TBA in AcOH (wt. %) | WHSV –hr |
|---|---|---|---|---|
| 1 | 140 | 2.35 | 0 | 1.35 |
| 2 | 104 | 1.22 | 10 | 1.1 |
| 3 | 104 | 1.53 | 25 | 1.16 |

| Run | % IB Conversion | Selectivity to t-butyl acetate % | Selectivity to DIB/TIB % | Selectivity to Higher C4's % |
|---|---|---|---|---|
| 1 | 94 | 24 | 28/10 | 38 |
| 2 | 88 | 89 | 11/0.2 | not detected |
| 3 | 77 | 97 | 3/trace | not detected |

ACOH is acetic acid
IB is isobutylene
TBA is t-butyl alcohol
TBAC is t-butyl acetate
DIB is diisobutylene
TIB is triisobutylene Run 1 is comparative and shows the high dimer make when no selectivity enhancing modifier is used.

Runs 2 and 3 in accordance with the invention demonstrate the dramatic effect on reaction selectivity of the t-butyl alcohol modifier.

TABLE 2

| Run | Reaction Temperature (° F.) | Reactant Ratio HOAC/IB (mol/mol) | Modifier % TBA in HOAC (wt %) | WHSV hr$^{-1}$ |
|---|---|---|---|---|
| 4 | 120 | 1.1 | 0% | 29 |
| 5 | 80 | 1.2 | 0% | 32 |
| 6 | 120 | 8.8 | 0% | 75 |
| 7 | 80 | 8.5 | 0% | 73 |
| 8 | 120 | 7.6 | 10% | 73 |
| 9 | 80 | 7.4 | 9% | 71 |
| 10 | 80 | 8.3 | 10% | 10 |
| 11 | 60 | 8.3 | 10% | 10 |
| 12 | 80 | 15.4 | 10% | 17 |
| 13 | 60 | 5.1 | 10% | 19 |
| 14 | 60 | 3.1 | 10% | 21 |

| | Conversion, % | | Selectivity % | | |
|---|---|---|---|---|---|
| Run | HOAC | IB | TBAC | DIB | TIB |
| 4 | 10% | 135% | 8.6% | 37.2% | 54.2% |
| 5 | 19% | 99% | 23.4% | 41.3% | 35.4% |
| 6 | 9% | 101% | 76.7% | 20.0% | 3.3% |
| 7 | 12% | 105% | 93.7% | 5.9% | 0.4% |
| 8 | 10% | 77% | 98.1% | 1.8% | 0.1% |
| 9 | 7% | 49% | 99.1% | 0.7% | 0.2% |
| 10 | 10% | 76% | 99.4% | 0.4% | 0.2% |
| 11 | 8% | 63% | 99.4% | 0.4% | 0.3% |
| 12 | 7% | 104% | 99.4% | 0.3% | 0.3% |
| 13 | 12% | 64% | 99.1% | 0.8% | 0.1% |
| 14 | 19% | 61% | 98.7% | 1.2% | 0.1% |

Runs 4–7 are comparative and show a gain in selectivity, even without a modifier, to ester at higher acid to olefin ratios. However, dimer make remains unacceptably high.

Runs 8–14 in accordance with the invention demonstrate the excellent results achieved through practice of the invention. As can be seen, the use of 9–10 wt % t-butyl alcohol based on acetic acid at varying mol ratios of acetic acid to isobutylene gave exceedingly good selectivities to ester with but minimal polymer make.

I claim:

1. In a continuous process for the reaction of isobutylene with acetic acid in the presence of a solid acidic catalyst to selectively form t-butyl acetate, the improvement which comprises carrying out the reaction at conditions effective to form t-butyl acetate in the presence of t-butanol in amount sufficient to enhance selectivity of the reaction to t-butyl acetate and to suppress isobutylene polymerization.

2. In a continuous process for the reaction of isobutylene with acetic acid in the presence of a solid anion exchange resin catalyst having sulfonic acid groups to selectively form t-butyl acetate, the improvement which comprises carrying out the reaction at conditions effective to form t-butyl acetate in the presence of t-butanol in amount sufficient to enhance selectivity of the reaction to t-butyl acetate and to suppress isobutylene polymerization.

* * * * *